(12) United States Patent
Leconte

(10) Patent No.: US 7,973,192 B2
(45) Date of Patent: Jul. 5, 2011

(54) PREPARATION OF BOTH HEXAMETHYLENE DIAMINE AND AMINOCAPRONITRILE

(75) Inventor: Philippe Leconte, Meyzieu (FR)

(73) Assignee: Rhodia Operations, Aubervilliers (FR)

( * ) Notice: Subject to any disclaimer, the term of this patent is extended or adjusted under 35 U.S.C. 154(b) by 354 days.

(21) Appl. No.: 12/090,125

(22) PCT Filed: Oct. 16, 2006

(86) PCT No.: PCT/FR2006/002320
§ 371 (c)(1),
(2), (4) Date: Aug. 20, 2008

(87) PCT Pub. No.: WO2007/045750
PCT Pub. Date: Apr. 26, 2007

(65) Prior Publication Data
US 2008/0319220 A1  Dec. 25, 2008

(30) Foreign Application Priority Data

Oct. 18, 2005 (FR) ...................................... 05 10588

(51) Int. Cl.
*C07C 255/00* (2006.01)
(52) U.S. Cl. ......................... 558/459; 564/463; 564/511
(58) Field of Classification Search .................. 558/459; 564/463, 511
See application file for complete search history.

(56) References Cited

U.S. PATENT DOCUMENTS

| 5,717,090 A * | 2/1998 | Bassler et al. ................ 540/539 |
| 6,384,283 B1 | 5/2002 | Leconte |
| 2007/0118001 A1 | 5/2007 | Bocquenet et al. |

FOREIGN PATENT DOCUMENTS

| EP | 1077932 B1 | 2/2001 |
| WO | WO 03/062188 A2 | 7/2003 |

* cited by examiner

*Primary Examiner* — Rei-tsang Shiao
(74) *Attorney, Agent, or Firm* — Buchanan Ingersoll & Rooney, P.C.

(57) ABSTRACT

Hexamethylenediamine and aminocapronitrile are simultaneously produced by hemihydrogenation of adiponitrile, which includes a stage of separation of the hexamethylenediamine from the hydrogenate by distillation of the hexamethylenediamine, the distillation of the hexamethylenediamine being carried out from the hydrogenate containing a free acid and/or an alkali metal or ammonium acid salt, whereby a top fraction A recovered at the column top of the stage of distillation of the hexamethylenediamine is essentially crude hexamethylenediamine and a small amount of THA; the amount of THA (tetrahydroazepine) present in the crude hexamethylenediamine constitutes a small proportion of the THA present in the hydrogenate.

13 Claims, No Drawings

PREPARATION OF BOTH HEXAMETHYLENE DIAMINE AND AMINOCAPRONITRILE

CROSS-REFERENCE TO PRIORITY/PCT APPLICATIONS

This application claims priority under 35 U.S.C. §119 of FR 0510588, filed Oct. 18, 2005, and is a continuation of PCT/FR 2006/002320, filed Oct. 16, 2006 and designating the United States (published in the French language on Apr. 26, 2007, as WO 2007/045750 A1; the title and abstract were also published in English), each hereby expressly incorporated by reference in its entirety and each assigned to the assignee hereof.

The invention relates to a process for the joint manufacture of hexamethylenediamine and of aminocapronitrile.

It relates more particularly to a process for the simultaneous manufacture of hexamethylenediamine and of aminocapronitrile by hemihydrogenation of adiponitrile.

Hexamethylenediamine and aminocapronitrile are important compounds used in particular as monomers or intermediates in the manufacture of polymers, in particular the manufacture of polyamides.

Hexamethylenediamine, used in particular for the synthesis of polyamide 6,6 or poly(hexamethylene adipamide), is generally obtained by complete hydrogenation of adiponitrile, followed by purification by distillation.

For many years, it has been known that hexamethylenediamine and aminocapronitrile can be obtained jointly by controlling the degree of progression of the hydrogenation of adiponitrile. Thus, several processes for the partial hydrogenation of adiponitrile have been provided which make it possible to obtain a mixture of hexamethylenediamine and of aminocapronitrile with concentrations of each of these compounds which can vary within wide proportions.

This stage of incomplete hydrogenation, also referred to as hemihydrogenation, can be carried out with highly varied conditions. For example, Patents EP 1 216 095, EP 0 801 647, EP 741 873, EP 927 157, EP 1 058 677 and EP 876 341 disclose a hemihydrogenation process carried out in the presence in particular of ammonia and of a solvent, such as an alcohol. Patents EP 0 797 568, EP 1 032 558, EP 1 077 932, EP 1 127 047, EP 1 165 498, EP 1 265 845, EP 1 397 345 and EP 1 397 346 disclose the use of a hemihydrogenation process in the presence of water, of a hydrogenation catalyst and of a strong base.

During this hydrogenation reaction, certain by-products are formed, such as tetrahydroazepine, referred to in the technical field as THA, and derivatives of this by-product.

These by-products, and more particularly THA, have to be separated in order to obtain a very low THA concentration in the compounds used as monomers for the manufacture of polymers and more particularly of polyamides.

Thus, it is necessary to recover and produce hexamethylenediamine which observes the purity specifications required for in particular its use as monomer in the manufacture of polyamide 6,6. One of these specifications relates to the maximum concentration of THA, which has to be less than 15 ppm.

One of the aims of the present invention is to provide a process which makes it possible to recover and produce, from the adiponitrile hemihydrogenation medium, referred to hereinafter as hydrogenate, a crude hexamethylenediamine exhibiting the lowest possible THA concentration in order to make possible the use of a purification producing a hexamethylenediamine in accordance with the specifications.

To this end, the invention relates to a process for the simultaneous manufacture of hexamethylenediamine and of aminocapronitrile by hemihydrogenation of adiponitrile. This process comprises a stage of separation of the hexamethylenediamine from the hydrogenate by distillation of the hexamethylenediamine.

According to the invention, the distillation of the hexamethylenediamine is carried out from the hydrogenate comprising a free acid and/or an alkali metal or ammonium acid salt.

According to the invention, the top fraction A recovered at the column top of the stage of distillation of the hexamethylenediamine comprises essentially crude hexamethylenediamine with a small amount of THA. The amount of THA present in the crude hexamethylenediamine represents a small proportion of the THA present in the hydrogenate.

The presence of $H^+$ ions in the hydrogenate makes it possible to limit the amount of THA distilled with the hexamethylenediamine by promoting in particular the formation of "heavy" compounds and thus to maintain a large part of the THA present in the hydrogenate in the bottom fraction B of the said column.

The amount of acid and/or of alkali metal or ammonium acid salt added to or present in the hydrogenation medium depends on the hemihydrogenation medium.

Thus, in the case where the hemihydrogenation reaction has been carried out in the presence of a catalyst, of water and of a strong base, the amount of acid added must make it possible, on the one hand, to neutralize the strong base and, on the other hand, to obtain a concentration of $H^+$ ions which is sufficient to limit the amount of THA distilling with the hexamethylenediamine. In this embodiment, the amount of acid and/or of acid salt added is determined in order to obtain a concentration of $H^+$ ions which is sufficient to obtain the distillation of a small part of the THA with the hexamethylenediamine. This concentration will be sufficient if the ratio T defined below is greater than 1.

The ratio T is determined by the following formula (I):

$$T = [A] \times n_a / [M] \times n_b \qquad (I)$$

in which:
[A] represents the molar concentration of anion corresponding to the acid or to the acid salt,
[M] represents the molar concentration of cation corresponding to the base present and to the acid salt,
$n_a$ represents the charge number of the anion A,
$n_b$ represents the charge number of the cation M.

The ratio T is preferably between 1.01 and 5, advantageously between 1.2 and 3.

This ratio T can be determined by calculating the amount of acid added to the hydrogenate as a function of the amount of base soluble in the hydrogenate. It is also possible to determine this ratio by determining the concentration of cation M and that of anion A associated with the acid added by analysis, in particular by conventional spectrometric methods.

In this embodiment, the alkali metal acid salt is preferably formed in situ by reaction of the acid with the base present in the hydrogenate.

In the case where the hemihydrogenation reaction is carried out in the absence of a base, the amount of acid or of salt added will make it possible solely to obtain a concentration of $H^+$ ions suitable for limiting the distillation of the THA with the hexamethylenediamine.

According to the invention, the suitable acids are, for example, inorganic acids, such as sulphuric acid, phosphoric acid, phosphorous acid or hydrochloric acid, or organic acids, such as, for example, aliphatic, cycloaliphatic or aromatic carboxylic acids, which may be mono- or polyfunctional, or aliphatic, cycloaliphatic or aromatic sulphonic acids. Mention may be made, as nonlimiting examples of organic acids, of acetic acid, propionic acid, valeric acid, hexanoic acid, adipic acid, terephthalic acid, glutaric acid, succinic acid, methylgluratic acid, ethyl-succinic acid, para-toluenesulphonic acid, methanesulphonic acid or fluoromethanesulphonic acid. Use may also be made of acid resins, in particular resins comprising sulphonic groups.

Mention may be made, as alkali metal or ammonium acid salts suitable for the invention, of the sodium, potassium or ammonium acid salts of the abovementioned acids. Mention may be made, as preferred examples, of sodium hydrogensulphate, potassium hydrogensulphate and ammonium hydrogensulphate.

In a preferred embodiment of the invention, sulphuric acid and alkali metal hydrogensulphates are preferred.

According to another preferred characteristic of the invention, the top fraction A recovered by distillation of the hexamethylenediamine from the hydrogenate is subjected to a further distillation eventually in presence of a strong base with base concentration disclosed here below, which makes it possible to recover, as top fraction C, the compounds exhibiting a boiling point lower than that of hexamethylenediamine, such as 1,2-diaminocyclohexane (DCH) and 2-aminomethylcyclopentylamine (AMCPA). The bottom fraction $A_1$ is composed essentially of hexamethylenediamine.

According to a preferred embodiment of the invention, this bottom fraction $A_1$ is subjected to a further distillation in the presence, optionally, of a strong base, such as potassium hydroxide or sodium hydroxide. The base concentration by weight in the bottom fraction $A_1$ or top fraction A in between 0.01 g/Kg of fraction $A_1$ or A and 1 g/Kg of fraction $A_1$ or A.

In this further distillation, the top fraction $A_2$ is composed of hexamethylenediamine with a high degree of purity corresponding to the specifications required in particular for use in the manufacture of polymers, such as polyamides. The bottom fraction $C_1$ comprises hexamethylenediamine and heavy compounds, including the THA derivatives.

This bottom fraction $C_1$ can advantageously be recycled to the hemihydrogenation stage, either in the hemihydrogenation reactor or to the stage of conditioning the catalyst, when this stage exists.

The process of the invention thus makes it possible to recover, from the adiponitrile hemihydrogenation medium, hexamethylenediamine with a high degree of purity, in particular with a very low THA content.

The various distillations described above are carried out in conventional distillation devices, such as plate columns, packed columns and the like. The operating temperature and pressure conditions for these columns are set by application of the simulation models and rules conventionally used by a person skilled in the art.

Thus, the distillations are preferably carried out at a pressure below atmospheric pressure, preferably of less than 300 mbar, advantageously at a pressure of between 10 and 100 mbar.

The number of plates in each column is also determined according to the degree of separation desired and by application of the rules and models used in the field of distillation.

Generally, the columns used have a number of theoretical plates of between 10 and 100, advantageously between 50 and 100.

According to a preferred embodiment of the invention, the bottom fraction B obtained by distillation of the hexamethylenediamine is subjected to a further distillation in order to recover a top fraction $B_1$ composed essentially of aminocapronitrile and a bottom fraction D composed essentially of adiponitrile and of compounds with a higher boiling point, including the THA derivatives.

This bottom fraction D is subjected to a further distillation in order to recover, in the form of a top fraction $D_1$, the adiponitrile and, in the form of a bottom fraction E, the compounds with a high boiling point and the inorganic salts formed by reaction between the acid and the base. Advantageously, the top fraction $D_1$ is recycled to the hemihydrogenation stage, while the bottom fraction E forms an effluent to be discharged.

Like the distillation of the hexamethylenediamine, these distillations are carried out in distillation columns conventionally used for the separation of organic compounds with different boiling points. The operating and size parameters are determined by use of the rules and models available to a person skilled in the art.

Thus, the operating pressure of the columns is advantageously less than 300 mbar. In a preferred embodiment, and in order to prevent the formation of heavy products and of light products by decomposition of the adiponitrile, the temperature of the various column bottoms is advantageously less than or equal to 185° C., preferably less than or equal to 180° C.

The process for the simultaneous manufacture of hexamethylenediamine and of amino-capronitrile of the invention makes it possible to recover, in a simple and economic way, a hexamethylenediamine with a high degree of purity, in particular by distilling the latter under conditions which favour the maintenance of the THA in the bottom fraction B, that is to say in the fraction comprising the aminocapronitrile.

Furthermore, the process of the invention makes it possible to remove the heavy products at the stage of distillation of the AdN exclusively.

Other details and advantages of the invention will become more clearly apparent in the light of the examples, which are given below solely by way of indication and without a limiting nature.

EXAMPLES

Tests on distilling and separating hexamethylenediamine from a medium obtained by hemihydrogenation of adiponitrile were carried out.

The hydrogenate has the following composition by weight:
HMD: 30.5%
ACN: 30.5%
AdN: 39%
The concentration of THA in the hydrogenate is 1100 ppm.
The hydrogenate is subjected to distillation in an adiabatic distillation column comprising 20 physical plates corresponding to 7 theoretical plates.

The distillation column operates under a pressure of 20 mbar with a column top temperature of 125° C. and a column bottom temperature of 170° C. The reflux ratio is equal to 2.

Three tests were carried out:
Test 1: in the absence of acid or of acid salt
Test 2: in the presence of 165 ppm of $KHSO_4$ (T=2)
Test 3: in the presence of 165 ppm of $KHSO_4$ and 65 ppm of $H_2SO_4$ (T=3.1)

The top fraction A was analysed in order to determine the percentage of the total THA present in the hydrogenate before distillation which has distilled with the hexamethylenediamine. The aminocapronitrile content of the top fraction was also determined.

|  | Test 1 | Test 2 | Test 3 |
|---|---|---|---|
| THA % | 21 | 12 | 9 |
| ACN % | 0 | 0 | 0 |

These results demonstrate that the presence of acid and/or of alkali metal acid salt leads to a reduction in the amount of THA which distills with the hexamethylenediamine.

The top fraction A recovered in Test 2 was subjected to continuous distillation with the operating parameters shown in the table below for the two columns:

|  | Topping column | Heavy-ends column |
|---|---|---|
| Number of stages installed | 71 packing stages | 65 bubble cap plates 75% efficiency |
| Operating pressure | 67 mbar | 67 mbar |
| Top temperature | 107° C. | 115° C. |
| Bottom temperature | 124° C. | 140° C. |
| Reflux ratio | >50 | 1 |
| Feed rate HMD | 2 kg/h | 2 kg/h |
| Potassium hydroxide, 10% |  | 2 g/h |
| Distillate rate | 0.015 kg/h | 1.9 kg/h |

The purified HMD recovered at the top of the heavy-ends column comprises less than 3 ppm of THA.

The invention claimed is:

1. A process for the preparation of both hexamethylenediamine and aminocapronitrile by hemihydrogenation of adiponitrile, the process comprising:
   (a) forming a hydrogenate by the hemihydrogenation of adiponitrile in the presence of a strong base;
   (b) adding to the hydrogenate an amount of acid and/or of alkali metal or ammonium acid salt, wherein the amount of acid and/or of alkali metal or ammonium acid salt added to the hydrogenate is determined to provide a ratio T, determined by the following formula (I):

$$T = [A] \times n_a / [M] \times n_b \quad (I)$$

in which:
   [A] represents the molar concentration of anion corresponding to the acid or to the acid salt,
   [M] represents the molar concentration of cation corresponding to the base present and to the acid salt,
   $n_a$ represents the charge number of the anion A,
   $n_b$ represents the charge number of the cation M, and
   T is greater than 1;
   (c) distilling the hydrogenate, which comprises an acid and/or an alkali metal or ammonium acid salt, and recovering a top fraction A, which comprises hexamethylenediamine, and a bottom fraction B, comprising aminocapronitrile, adiponitrile and high boiling point compounds.

2. The process as defined by claim 1, the hydrogenate comprising an acid selected from the group consisting of sulphuric acid, phosphoric acid, phosphorous acid, hydrochloric acid, an aliphatic, cycloaliphatic or aromatic carboxylic acid, whether mono- or polyfunctional, and an aliphatic, cycloaliphatic or aromatic sulphonic acid.

3. The process as defined by claim 1, the hydrogenate comprising an alkali metal or ammonium acid salt of an acid selected from the group consisting of sulphuric acid, phosphoric acid, phosphorous acid, hydrochloric acid, an aliphatic, cycloaliphatic or aromatic carboxylic acid, whether mono- or polyfunctional, and an aliphatic, cycloaliphatic or aromatic sulphonic acid.

4. The process as defined by claim 1, wherein said ratio T ranges from 1.01 to 5.

5. The process as defined by claim 1, wherein the top fraction A, essentially of hexamethylenediamine, is distilled to separate, as a top fraction C, compounds having a boiling point lower than that of hexamethylenediamine and to recover a bottom fraction $A_1$ essentially of hexamethylenediamine, and distilling said bottom fraction $A_1$ to recover a top fraction $A_2$ of purified hexamethylenediamine and a bottom fraction $C_1$.

6. The process as defined by claim 5, comprising adding a strong base to the bottom fraction $A_1$ or the top fraction A, before distillation thereof.

7. The process as defined by claim 6, said strong base comprising an alkali metal hydroxide.

8. The process as defined by claim 6, wherein the concentration by weight of strong base in the bottom fraction $A_1$ or top fraction A ranges from 0.01 g/kg of fraction $A_l$ or A to 1 g/kg of fraction $A_1$ or A.

9. The process as defined by claim 5, comprising recycling the bottom fraction $C_1$ into the hemihydrogenation reactor or into the hydrogenate.

10. The process as defined by claim 1, comprising distilling the bottom fraction B and recovering a top fraction $B_1$ of aminocapronitrile and a bottom fraction D of adiponitrile and high boiling point compounds.

11. The process as defined by claim 10, comprising distilling the bottom fraction D and recovering a top fraction $D_1$ of adiponitrile and a bottom fraction E of high boiling point compounds and inorganic salts formed by reaction between acid and base.

12. The process as defined by claim 11, comprising recycling the top fraction $D_1$ into the hemihydrogenation reactor.

13. The process as defined by claim 1, wherein said ratio T ranges from 1.2 to 3.

* * * * *